United States Patent [19]

Carter

[11] 4,038,332
[45] July 26, 1977

[54] SEPARATION OF ETHYL FLUORIDE

[75] Inventor: C. O. Carter, Bartlesville, Okla.

[73] Assignee: Phillips Petroleum Company, Bartlesville, Okla.

[21] Appl. No.: 621,097

[22] Filed: Oct. 9, 1975

[51] Int. Cl.² .............. C07C 19/08; C07C 21/18; C07C 21/20; C07C 21/22

[52] U.S. Cl. .................................. 260/653; 55/48; 55/71; 62/17; 62/20; 203/12; 203/42; 260/652 P; 260/683.42; 423/488

[58] Field of Search .......... 55/71, 47, 48, 50; 62/17, 20; 203/12, 34, 50, 42, 43, 45, 46, 39; 260/683.42, 683.48, 653, 652 P; 423/488

[56] References Cited

U.S. PATENT DOCUMENTS

| | | | |
|---|---|---|---|
| 2,759,032 | 8/1956 | Dixon | 260/683.42 |
| 3,204,010 | 8/1965 | Van Pool | 260/683.42 |
| 3,204,011 | 8/1965 | Hettick et al. | 260/683.42 |
| 3,751,517 | 8/1973 | Hutson et al. | 260/683.48 |
| 3,761,540 | 9/1973 | Hutson et al. | 260/683.51 |
| 3,763,265 | 10/1973 | Hutson et al. | 260/683.42 |
| 3,767,726 | 10/1973 | Hutson et al. | 260/683.42 |
| 3,767,727 | 10/1973 | Chapman | 260/683.48 |
| 3,825,616 | 7/1974 | Chapman | 260/683.48 |
| 3,864,423 | 2/1975 | Chapman | 260/683.42 |
| B 426,674 | 1/1975 | Chapman | 260/683.48 |

*Primary Examiner*—Bernard Nozick
*Assistant Examiner*—Frank Sever

[57] ABSTRACT

An overall process for the separation of ethyl fluoride from a propane stream containing same is provided wherein said propane stream is extractively distilled using HF, as the extractive solvent producing a first mixture consisting essentially of propane and HF and a second mixture consisting essentially of ethylfluoride and HF, and wherein this second mixture is then mixed with water followed by phase separation.

5 Claims, 1 Drawing Figure

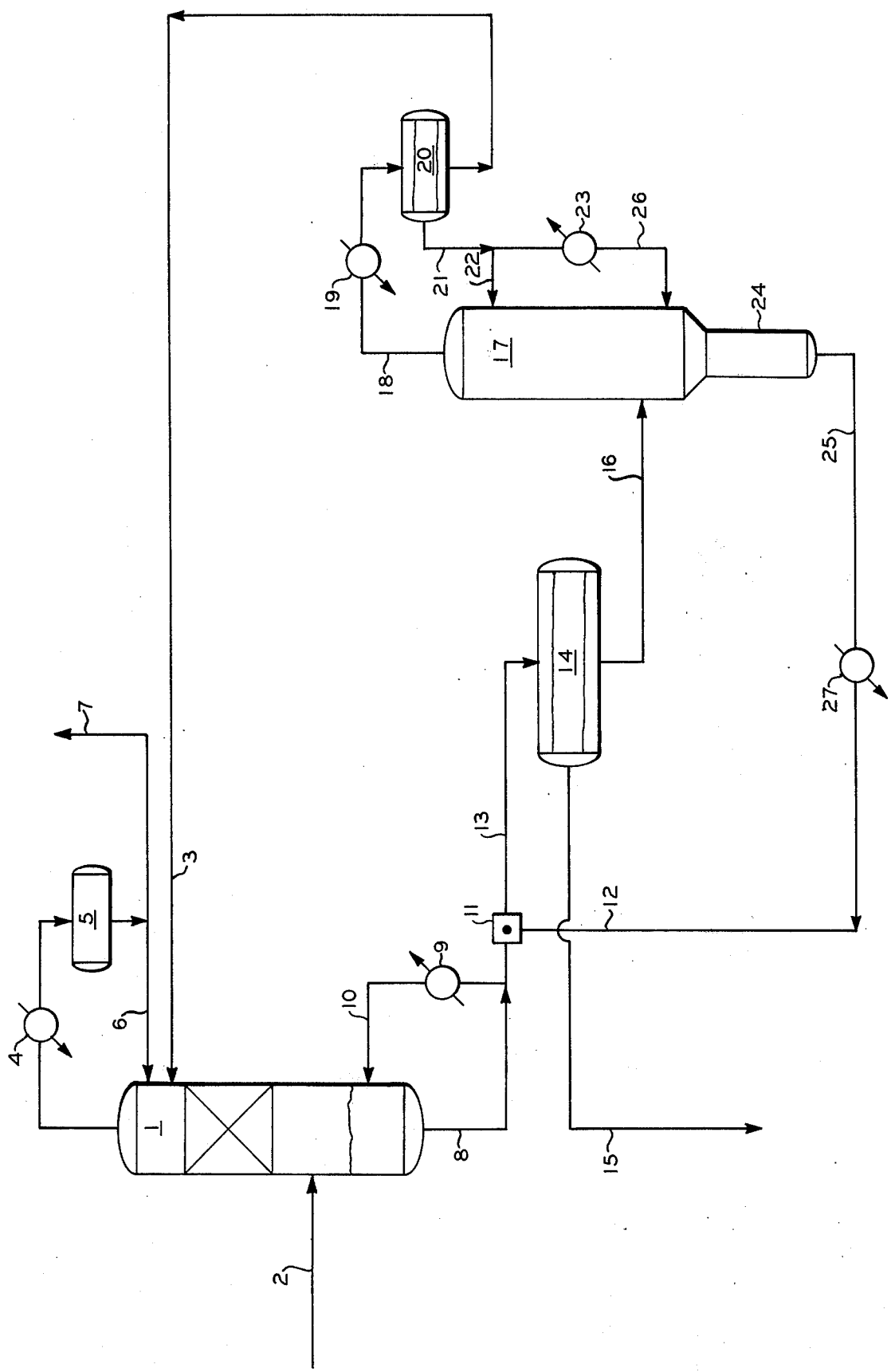

SEPARATION OF ETHYL FLUORIDE

This invention relates to the separation of mixtures containing ethyl fluoride. In one aspect this invention relates to the separation of a mixture of hydrogen fluoride and ethyl fluoride. In another aspect, this invention relates to the separation of ethyl fluoride from a mixture of propane and ethyl fluoride.

BACKGROUND OF THE INVENTION

High quality fuels can be produced by catalytic alkylation of hydrocarbons. In such a process an olefin and an isoparaffin are reacted in the presence of a hydrogen fluoride catalyst to produce an alkylate. In order to further improve the octane number of such alkylates, it has been found in recent years (e.g. U.S. Pat. No. 3,842,140) that ethyl fluoride can be advantageously employed in addition to the hydrogen fluoride in the alkylation reaction. During the alkylation a certain quantity of propane is withdrawn from the alkylation reaction zone together with the alkylate and, since propane and ethyl fluoride have very similar boiling points, a certain quantity of ethyl fluoride is admixed in the propane vapor leaving the depropanizing zone of an alkylation unit. Since the ethyl fluoride content of the propane is detrimental to the use thereof as a fuel, it has been proposed to extract the ethyl fluoride from propane by contacting the propane vapor stream containing ethyl fluoride with a liquid HF stream.

One of the problems arising in this process is that the mixture of ethyl fluoride and hydrogen fluoride produced by this extraction does not have a composition that allows a recycling of this mixture to the hydrogen fluoride alkylation unit. Therefore, it is necessary to separate the two components first. Furthermore, in some alkylation plants ethylene is not readily available. In such plants ethyl fluoride could, therefore, be used directly as an additive as explained to improve the octane number of the alkylate. Therefore, it would be desirable to have a process available in which relatively pure ethyl fluoride is produced that then could be used for the alkylation process.

THE INVENTION

It is thus one object of this invention to provide a process for separating ethyl fluoride from a mixture of ethyl fluoride and HF.

Another object of this invention is to provide a process for the separation and recovery of ethyl fluoride from a stream of propane containing ethyl fluoride.

These and other objects, advantages, embodiments, details and features of this invention will become apparent to those skilled in the art from the following detailed description of the invention, the appended claims and the drawing, which shows a schematic flow diagram of an alkylation and ethyl fluoride separation unit.

In accordance with this invention, I have now discovered that by adding water to a mixture of hydrogen fluoride and ethyl fluoride, there is formed a mixture that can be phase separated into a phase consisting essentially of ethyl fluoride and some HF, and a phase consisting essentially of HF and water.

The present invention, therefore, provides a method for separating ethyl fluoride from a mixture containing ethyl fluoride and HF, which method comprises contacting the mixture in a contacting zone with an aqueous extractant to produce a mixture containing ethyl fluoride, HF and water, and separating this mixture containing ethyl fluoride, HF and water into a first phase consisting essentially of ethyl fluoride and into a second phase consisting essentially of HF, aqueous extractant and ethyl fluoride, this second phase having a reduced ethyl fluoride content as compared to the feedstream.

One embodiment of this invention consists in a closed loop operation with the aqueous extractant. The second phase in this embodiment is separated into a dry HF stream containing essentially no water and into a water-comprising stream containing some HF and this water-comprising stream is mixed as the aqueous extractant with the ethyl fluoride/HF mixture. Thereby no polluted water is produced, but the water containing some HF is rather recycled.

The strong separating effect of rather small quantities of water in an ethyl fluoride/HF mixture is utilized in accordance with the presently preferred embodiment in the process for separating ethyl fluoride from propane. In accordance with this embodiment, a propane stream containing propane and ethyl fluoride is extracted in an extracting zone with an HF extractant being a dry HF stream containing essentially no water to produce an overhead stream containing propane and HF and being essentially free of ethyl fluoride, and a bottom stream containing ethyl fluoride and HF, and wherein this bottom stream is then introduced as the ethyl fluoride and HF containing mixture mentioned above into the contacting zone where it is contacted with the aqueous extractant as described above. Thereby a first phase rich in ethyl fluoride and a second of HF and water having a reduced ethyl fluoride content, as compared to the feedstream introduced into the contacting zone, are produced and readily separated. Advantageously, the second phase is separated into a dry HF stream containing essentially no water and into a water-comprising stream. This water-comprising stream is reintroduced into the contacting zone as the aqueous extractant, whereas the dry HF stream is reintroduced into the extracting zone as said HF extractant.

The separation of the second phase into a dry HF stream containing essentially no water and into a water-comprising stream mentioned above can be readily achieved by introducing the second phase into an HF rerun column. Advantageously, this rerun column is now operated by a reflux and reboil stream consisting essentially of ethyl fluoride and propane. The overhead of this rerun column is condensed and phase separated. The dry HF stream is withdrawn as a first (lower liquid) overhead phase from the phase separating zone. A stream consisting essentially of ethyl fluoride and propane is withdrawn as a second overhead (upper liquid) phase. This second overhead phase contains practically no water. A first portion of the second overhead phase is reintroduced as liquid via the top of the rerun column as a reflux stream, whereas a second portion of this second overhead phase is evaporated and reintroduced into the rerun column at a lower position below the locus of introduction of the second phase, which can also be described as a wet HF stream. From the bottom of the rerun column described, a liquid stream consisting essentially of water containing a small amount of HF is withdrawn. This aqueous stream is reintroduced into the contacting zone to produce the two phases, one being rich in ethyl fluoride, the second being lean in ethyl fluoride.

The single FIGURE shows the preferred embodiment of the invention.

The invention will be still more fully understood from the following description of the drawing. In the drawing schematically a process flow of a separating unit is shown. The yield portion of the overhead of a main fractionator in an HF alkylation plant (not shown) is passed to an extracting zone 1 via line 2. This extracting zone 1 is an ethyl fluoride tower into which a dry liquid HF stream is introduced via line 3. An overhead stream is withdrawn from the ethyl fluoride tower 1, passed through a condenser 4 and an accumulator vessel 5. A portion of the overhead stream is reintroduced as reflux and near the top of the ethyl fluoride tower 1 via line 6, whereas the yield quantity of the overhead stream consisting essentially of propane and HF is withdrawn via line 7 for further processing in an HF stripper (not shown) in which a propane stream being essentially free of HF is produced.

From the bottom of the ethyl fluoride tower 1, liquid stream 8 is withdrawn which consists essentially of ethyl fluoride and HF, and contains some water and some propane. A portion of this bottom stream, which is withdrawn via line 8, is reboiled in reboiler 9 and reintroduced near the bottom of the ethyl fluoride tower 1 via line 10.

The remainder of the bottom stream is introduced into a contactor 11. Into this contactor 11 also an aqueous stream is introduced via line 12. The admixed stream leaving the contactor 11 and consisting essentially of ethylene fluoride and HF, as well as some propane and an increased amount of water (as compared with stream 8), is introduced via line 13 to the settler 14. In this settler 14 a first phase, being rich in ethyl fluoride, is withdrawn via line 15. This stream also contains some HF and a very small amount of water, as well as some propane. A second phase being lean in ethyl fluoride and consisting essentially of HF and most of the water, together with some ethyl fluoride and some propane, is withdrawn via line 16 from the settler 14. This stream 16 of wet HF is introduced into a rerun column 17. A gaseous overhead stream is withdrawn from this column 17 via line 18. This overhead stream is condensed in condenser 19, and the condensed stream is passed to settler 20. From this settler 20, a dry HF phase 3 is withdrawn consisting essentially of liquid HF and a very small quantity of water. This dry HF phase is reintroduced via line 3 as the HF extractant into the ethyl fluoride tower 1.

A second phase consisting essentially of ethyl fluoride and propane, together with some HF and a very small quantity of water, is withdrawn via line 21 from the settler 20. A portion of this liquid phase withdrawn via line 21 is reintroduced via line 22 into the top portion of the rerun column 17 as a reflux stream. The other portion of the stream 21 is evaporated in heater 23 and reintroduced below the inlet for the wet HF stream 16 into the rerun column 17 as stripping vapor via line 26.

From the lower and smaller end 24 of the rerun column 17, a liquid stream consisting essentially of water and containing some HF is withdrawn via line 25. This water stream is cooled in cooler 27 and reintroduced into the contactor 11 via line 12.

Typical operating data for the separating units shown are given in the following table.

Table

| Ethyl Fluoride Tower (1) | | |
|---|---|---|
| Pressure, psig | 234 | (1600 KPa) |
| Temperature, °F | | |
| Top | 110 | (43.3 °C) |
| Bottom | 175 | (79.3 °C) |
| Settler (14) | | |
| Pressure, psig | 220 | (1500 KPa) |
| Temperature, °F | 110 | (43.3 °C) |
| Rerun (17) | | |
| Pressure, psig | 165 | (1130 KPa) |
| Temperature, °F | | |
| Top | 90 | (32.2 °C) |
| Bottom | 220 | (103.3 °C) |
| Settler (20) | | |
| Pressure, psig | 160 | (1100 KPa) |
| Temperature, °F | 90 | (32.2 °C) |

It is presently preferred to keep the temperature of ethyl fluoriderich stream low enough not to exceed 175° F (79.3° C), thereby the polymerization of ethyl fluoride in HF acid is minimized. Therefore, it is particularly advantageous to operate the ethyl fluoride tower in which an ethyl fluoriderich bottom stream is separated from a propane/HF/ethyl fluoride mixture at or below 175° F (79.3°. C). The ethyl fluoride tower can be operated without a reboiler.

The invention will still be more fully understood from the following calculated example showing the material balance of a separation of ethyl fluoride from propane stream containing ethyl fluoride.

EXAMPLE I

Into an ethyl fluoride tower as shown in the drawing under item 1, a liquid stream consisting essentially of propane, HF, ethyl fluoride, and a very small quantity of water is introduced. This stream is extracted in this ethyl fluoride tower 1 by a dry HF stream consisting essentially of HF and a small quantity of water. The quantities of various components in the different streams shown in the drawing are given in the following table. This table does not show a material balance for the alkylation unit 10, the settler 20, and the main separator 30. Since these units are as such known in the art and are operated in a known manner, the flow of materials through these units is not shown in the table.

| | Material Balance of Ethyl Fluoride Separation Gallons/Hour | | | | | | | | |
|---|---|---|---|---|---|---|---|---|---|
| Stream No. | 2 | 7 | 8 | 3 | 12 | 15 | 16 | 22 | 26 |
| Component | | | | | | | | | |
| Propane | 1246 | 976 | 582 | 317 | — | 270 | 317 | 12425 | 38062 |
| HF | 1218 | 5 | 32888 | 31675 | 24 | 1213 | 31699 | 396 | 1216 |
| $C_2H_5F$ | 6738 | T | 7428 | 690 | — | 6738 | 690 | 27125 | 83562 |
| $H_2O$ | 12 | T | 392 | 380 | 1288 | 12 | 1668 | 4 | 12 |

The material balance calculated above for an alkylation unit producing 5000 barrels per day (800 cubic meters/day) of alkylate shows that, by the closed loop system described, in a very advantageous manner the propane stream can be freed of essentially all the ethyl fluoride contained in such a stream, and that by the water treatment of the HF/ethyl fluoride stream, the HF is effectively separated from the ethyl fluoride.

EXAMPLE II

This example is given to show the strong influence of water on the solubility of ethyl fluoride in HF. During the operation of an alkylation pilot plant the recycle acid has been analyzed. The results of these analyses are shown in the following table.

Table

| Acid temperature (° F) | 80 | 79 | 79 | 78 |
|---|---|---|---|---|
| Acid composition (weight %) | | | | |
| Water | 0.9 | 1.5 | 3.7 | 3.8 |
| HF | 74.6 | 75.1 | 72.6 | 78.3 |
| Acid soluble oils | 4.7 | 3.9 | 4.2 | 6.6 |
| Ethyl fluoride | 13.9 | 9.0 | 2.0 | 1.7 |
| Weight ratio of ethyl fluoride to HF: | 0.187 | 0.120 | 0.028 | 0.022 |

Thus the weight ratio of ethyl fluoride to HF of about 0.2 in a mixture with water, and a water to HF weight ratio of about 0.01, is lowered to a value of about 0.02 to 0.03 when the water content of such a mixture is raised to a water to HF weight ratio of about 0.05.

Reasonable variations and modifications, which will become apparent to those skilled in the art, can be made in this invention without departing from the spirit and scope thereof.

I claim:

1. A process for separating ethyl-fluoride from an ethyl fluoride containing propane stream comprising
   a. introducing said ethyl fluoride containing propane stream into an ethyl fluoride extraction zone,
   b. introducing a dry liquid HF stream into said ethyl fluoride extraction zone to extract ethyl fluoride from said ethyl fluoride containing propane stream,
   c. withdrawing a first stream comprising propane and being essentially free of ethyl fluoride from said ethyl fluoride extraction zone,
   d. withdrawing a second stream comprising ethyl fluoride and HF from said ethyl fluoride extraction zone,
   e. mixing said second stream with an aqueous extractant consisting esentially of to form mixture, and
   f. separating said mixture into a first phase consisting essentially of ethyl fluoride and into a second phase consisting essentially of HF and water.

2. A process in accordance with claim 1 comprising fractionally distilling said second phase to form a dry HF stream and a water stream.

3. A process in accordance with claim 2 comprising recycling said water stream as said extractant in step e, and recycling said dry HF stream into said ethyl fluoride extraction zone in step (b).

4. A method for separating ethyl fluoride from a first mixture consisting essentially of ethyl fluoride and HF, which comprises
   a. contacting said first mixture with an aqueous extractant consisting essentially of water to produce a second mixture consisting essentially of ethyl fluoride, HF and said aqueous extractant and,
   b. phase separating said second mixture into a first phase consisting essentially of ethyl fluoride, and into a second phase consisting essentially of HF and water.

5. The method of claim 4 also including the steps of
   a. fractionating said second phase into a dry HF stream and into a water comprising stream, and
   b. utilizing said water-comprising stream as said aqueous extractant for said first mixture.

* * * * *

UNITED STATES PATENT AND TRADEMARK OFFICE
CERTIFICATE OF CORRECTION

PATENT NO. : 4,038,332
DATED : July 26, 1977
INVENTOR(S) : Cecil O. Carter

It is certified that error appears in the above-identified patent and that said Letters Patent are hereby corrected as shown below:

Column 6, line 5, --- water,--- should be inserted after "of";
--- a --- should be inserted after "form".

Signed and Sealed this

Fourteenth Day of March 1978

[SEAL]

Attest:

RUTH C. MASON
*Attesting Officer*

LUTRELLE F. PARKER
*Acting Commissioner of Patents and Trademarks*